(12) United States Patent
Springer

(10) Patent No.: US 7,799,945 B2
(45) Date of Patent: Sep. 21, 2010

(54) CATALYTIC PROCESS FOR PREPARING ALIPHATIC STRAIGHT-CHAIN AND β-ALKYL-BRANCHED CARBOXYLIC ACIDS

(75) Inventor: Helmut Springer, Dinslaken (DE)

(73) Assignee: Oxea Deutschland GmbH, Oberhausen (DE)

( * ) Notice: Subject to any disclaimer, the term of this patent is extended or adjusted under 35 U.S.C. 154(b) by 621 days.

(21) Appl. No.: 11/787,868

(22) Filed: Apr. 18, 2007

(65) Prior Publication Data
US 2007/0265467 A1    Nov. 15, 2007

(30) Foreign Application Priority Data
May 12, 2006    (DE) ................. 10 2006 022 168

(51) Int. Cl.
*C07C 51/235* (2006.01)
(52) U.S. Cl. ................... 562/531; 562/534
(58) Field of Classification Search ........... 562/531, 562/534
See application file for complete search history.

(56) References Cited

U.S. PATENT DOCUMENTS 6,800,783 B2 * 10/2004 Springer et al. ............ 562/531

FOREIGN PATENT DOCUMENTS

| DE | 100 10 771 C1 | 5/2001 |
| DE | 10 2004 055 252 A1 | 5/2006 |
| GB | 856 962 A | 12/1960 |

\* cited by examiner

*Primary Examiner*—Taylor Victor Oh
(74) *Attorney, Agent, or Firm*—Charles A. Muserlian

(57) ABSTRACT

A catalytic process for preparing aliphatic straight-chain and β-alkyl-branched carboxylic acids of 5 to 13 carbon atoms by catalytic oxidation of the corresponding aldehydes by means of oxygen or oxygen-containing gas mixtures in the liquid phase in the presence of a catalyst system contains alkali metal carboxylates or alkaline earth metal carboxylates or a mixture thereof in an amount, calculated as alkali metal or alkaline earth metal, of 0.5 mmol to 15 mmol per mol of aldehyde used and also metals of groups 4 to 12 of the Periodic Table of the Elements, cerium or lanthanum in amounts of not more than 5 ppm, based on the aldehyde used, or compounds of such metals, with the catalyst system being the reaction product from an aldehyde oxidation reaction.

18 Claims, No Drawings

CATALYTIC PROCESS FOR PREPARING ALIPHATIC STRAIGHT-CHAIN AND β-ALKYL-BRANCHED CARBOXYLIC ACIDS

The present invention relates to a novel, catalytic process for preparing aliphatic straight-chain and β-alkyl-branched carboxylic acids from aldehydes by oxidation using oxygen or oxygen-containing gases.

Aldehydes are widely used as starting materials for the preparation of carboxylic acids. The predominant position occupied by aldehydes for this application is due to their good availability from a number of processes, including processes utilized in industry. In addition, the carbonyl group of aldehydes can easily be converted into the carboxyl group. In processes carried out in industry, the conversion of aldehydes into carboxylic acids is predominantly carried out in the presence of catalysts. Possible catalysts are predominantly salts of transition metals, in particular salts of cobalt and of manganese and also of chromium, iron, copper, nickel, silver and vanadium. Nevertheless, the formation of carboxylic acids from aldehydes is frequently associated with secondary and decomposition reactions, even when optimal temperature conditions are adhered to.

J. Prakt. Chem. vol. 14 (1961), 71-83 describes the oxidation of isononanal in the presence of cobalt acetate or manganese naphthenate. In the presence of the manganese-containing catalyst, the yield of isononanoic acid at a reaction temperature of 60° C. is only about 70%.

In the process described in DE-A 30 29 700, aliphatic monocarboxylic acids having from 6 to 9 carbon atoms are prepared by oxidizing the corresponding aldehydes by means of oxygen in pure form or by means of air. A combination of manganese and copper compounds which are soluble in the acid acts as catalyst. The metals are present in an amount in each case of from about 10 to about 2000 ppm, preferably from 200 to 600 ppm of manganese and copper, based on the weight of the liquid reaction mixture. The molar ratio of manganese to copper is from 5:1 to 0.5:1. The reaction of the starting materials is carried out in the liquid phase at temperatures of from about 50 to 80° C. and pressures in the range from about 1.4 to 10.3 bar. The process description indicates that the presence of copper and manganese compounds in the reaction product, i.e. in the carboxylic acid, is the main difficulty associated with this process. Removal of the metals requires complicated purification measures, for example precipitation of the metals using aqueous oxalic acid.

The process disclosed in U.S. Pat. No. 4,487,720 for preparing $C_5$- to $C_9$-monocarboxylic acids by oxidation of aldehydes having the same number of carbon atoms by means of pure oxygen or by means of air is likewise carried out using copper and manganese compounds as catalysts. The total amount of the metals extends over a range from 10 to 200 ppm, based on the total weight of the solution comprising aldehyde, acid and catalyst. Manganese and copper are used in a molar ratio of from about 3:1 to about 1:1. A disadvantage of this procedure is said to be the formation of copper films which occur in the purification of the acid by distillation and result in mechanical damage in the distillation apparatus. To avoid this problem, it is recommended that the distillation be carried out in the presence of oxygen.

The published German patent application 26 04 545 describes the preparation of alkylcarboxylic acids of the formula $C_nH_{2n+1}COOH$, where n is from 2 to 18, by hydroformylation, also known as the oxo process, of an olefin of the formula $C_nH_{2n}$ and direct oxidation of the reaction mixture obtained in the hydroformylation. In this context, "direct" means that no prior work-up of the hydroformylation mixture is carried out and the subsequent oxidation reaction is carried out in the presence of rhodium. The known oxidation process is employed, in particular, for the preparation of mixtures of isomeric $C_9$-$C_{16}$-fatty acids. Starting olefins for the oxo process are preferably the dimers and trimers of propene and of the butenes, including, in particular, dimeric isobutene (2,4, 4-trimethyl-1-pentene). Both individual reactions of the two-stage process, i.e. both the hydroformylation and the oxidation, are catalyzed by rhodium in the form of its compounds. The rhodium concentration in the reaction mixture subjected to the oxidation is therefore determined by the relatively high rhodium content of the hydroformylation product. To ensure that the overall process is economical, it is necessary to recover the noble metal as completely as possible from the end product of the process, viz. the carboxylic acid, by means of suitable measures. In addition, it cannot be ruled out that rhodium in the prevailing concentration will promote undesirable secondary reactions during the oxidation step, since the carboxylic acid yield is, as the examples show, unsatisfactory for industrial utilization of the process.

In J. Org. Chem. 1990, 55, p. 1563 ff., LARKIN reports that the presence of catalysts in the commercial oxidation of aldehydes to carboxylic acids is considered necessary because traces of metal salts which can catalyze secondary reactions are present in the reaction mixture. The formation of the metal salts is due to corrosion of metallic plant components. The function of the catalysts is to overcompensate the action of the corrosion products.

In Ullmanns Encyklopädie der technischen Chemie, 4th edition 1975, vol. 9, reference is also made a number of times to the negative influence of metallic impurities in the starting aldehydes used for the oxidation. For example, in the oxidation of butyraldehyde to butyric acid, iron and cobalt salts dissolved in the butyraldehyde lead to increased formation of by-products (l.c., page 142, left-hand column), and in the oxidation of 2-ethylhexanal to 2-ethylhexanoic acid, heavy metal ions accelerate the decarbonylation of the starting aldehyde to form heptane (l.c., page 144, left-hand column).

It is indicated in the prior art that the action of catalyst additives depends on the structure of the aldehyde used for the oxidation. Thus, for example, DE 950 007 discloses that the oxidation of aldehydes which are branched in the α position requires the addition of small amounts of alkali metal salts of carboxylic acids in order to obtain the desired carboxylic acids in high yield and at the same time in high purity.

According to the teachings of the published Japanese patent application 53-105413, α-branched aliphatic aldehydes are oxidized by means of oxygen in the presence of lithium compounds or alkaline earth metal compounds which are used in amounts of from 0.01 to 10% by weight (based on the total reaction system) in order to prepare α-branched aliphatic carboxylic acids.

A key aspect of the procedure described in the French patent application 2 769 624 is adherence to relatively low reaction temperatures, namely temperatures in the range from 0 to 25° C. The process likewise requires the presence of alkali metal compounds or alkaline earth metal compounds as auxiliaries. The specific effects displayed by these compounds is not disclosed, i.e. whether they, as is known, merely improve the selectivity of the reaction or else possibly also increase the reaction rate at the low temperatures selected remains unanswered.

In the oxidation of α-branched aldehydes in which the carbon atom adjacent to the carbonyl carbon bears the branch, the prior art thus recommends the addition of small amounts of alkali metal carboxylates to improve the selectivity. However, such an addition is associated with an increase in the reaction time because of its inhibiting action. Among α-branched aldehydes, 2-ethylhexanal which is converted in large quantities into 2-ethylhexanoic acid is of particular economic importance.

The oxidation of aldehydes which bear the branch in the β position, i.e. on the carbon atom which is the next but one carbon atom from the carbonyl carbon, can likewise be effected with addition of a catalyst. An economically important aldehyde having a high proportion of β-alkyl-branched compounds is obtained by hydroformylation of industrially available diisobutene (2,4,4-trimethyl-1-pentene). Oxidation in the presence of rhodium as described in DE-A1-26 04 545 gives a mixture of isomeric $C_9$-fatty acids having a high proportion of 3,5,5-trimethylhexanoic acid, frequently also referred to as isononanoic acid. The oxidation of β-alkyl-branched aldehydes, for example of isovaleraldehyde, in the presence of alkali metal carboxylates or alkaline earth metal carboxylates is known from DE-A1-732 720.

According to the teachings of DE-C1-100 10 771, linear aldehydes can be converted into the corresponding carboxylic acids in the presence of transition metals or compounds thereof.

The patent DE-C1-100 10 771 likewise discloses the use of a mixture of alkali metal salts and transition metals in the oxidation of 2-methylbutanal as α-branched aldehyde.

GB 856,962 discloses an oxidation process for preparing saturated aliphatic monocarboxylic acids, which is carried out in the presence of a mixture of cobalt salts and/or manganese salts with alkali metal or alkaline earth metal salts, with the addition of alkali metal or alkaline earth metal countering oxidative degradation. An example described is the oxidation of propionaldehyde in which cobalt or manganese or a mixture thereof is present in an amount of from 0.00001 to 1.0 mol per mol of propionaldehyde.

The as yet unpublished German patent application number 10 2004 055 252.5-44 is concerned with the catalytic oxidation of aliphatic straight-chain and β-alkyl-branched aldehydes having from 5 to 13 carbon atoms to the corresponding carboxylic acids. A characteristic of this catalytic oxidation process is the use of a catalyst system comprising a mixture of alkali metal or alkaline earth metal carboxylates in an amount of 1-10 mmol, calculated as alkali metal or alkaline earth metal, per mol of aldehyde used and from 0.1 to 5.0 ppm of a metal of groups 5 to 11 of the Periodic Table of the Elements or its compounds or a mixture of such metals or their compounds. The ppm figures given, calculated as transition metal, are based on the aldehyde used.

It has now surprisingly been found that the oxidation process according to the German patent application 10 2004 055 252.5-44 can be improved further in respect of the aldehyde conversion into the corresponding carboxylic acids at high selectivity when the catalyst system comprising the mixture of alkali metal or alkaline earth metal carboxylates and transition metals of groups 5 to 11 of the Periodic Table of the Elements is used not as fresh catalyst but as reaction product from an aldehyde oxidation reaction. The preparation of this reaction product in an aldehyde oxidation reaction can also be regarded as preforming or activation of the catalyst system. After the aldehyde oxidation reaction is complete, the carboxylic acids formed, unreacted starting aldehyde and further volatile constituents are separated off by distillation and the distillation residue containing the reaction product is used for the actual aldehyde oxidation reaction.

Furthermore, it has surprisingly been found that the advantageous effect of the preforming of the catalyst system on the oxidation behavior of aldehydes is not restricted merely to a catalyst system containing alkali metal or alkaline earth metal carboxylates and transition metals of groups 5 to 11 of the Periodic Table but is also observed in the case of catalyst systems containing metals or metal compounds of groups 4 and 12 of the Periodic Table of the Elements and cerium or lanthanum.

The present invention accordingly provides a catalytic process for preparing aliphatic straight-chain and β-alkyl-branched carboxylic acids having from 5 to 13 carbon atoms by oxidation of the corresponding aldehydes by means of oxygen or oxygen-containing gas mixtures at from 20 to 100° C. in the liquid phase, wherein the oxidation of the aldehydes is carried out in the presence of a catalyst system which is the reaction product from an aldehyde oxidation reaction in which the aldehyde oxidation reaction is carried out in the presence of alkali metal carboxylates or alkaline earth metal carboxylates or a mixture thereof in an amount, calculated as alkali or alkaline earth metal, of from 0.5 mmol to 5 mmol per mol of aldehyde used and of from 0.05 to 5.0 ppm of a metal of groups 4 to 12 of the Periodic Table of the Elements, cerium or lanthanum or the corresponding amount of a compound of such a metal or a mixture of such metals and/or metal compounds, based on the aldehyde used.

Surprisingly, aliphatic straight-chain or β-alkyl-branched aldehydes can be reacted with pure oxygen or oxygen-containing gas mixtures to form the corresponding carboxylic acids at high selectivity combined with an increased conversion if the procedure is carried out in the presence of a catalyst system which contains small amounts of alkali metal carboxylates or alkaline earth metal carboxylates and small amounts of selected metals or compounds of these metals and is the reaction product of an aldehyde oxidation reaction.

An essential feature of the novel process is the use of a catalyst system containing alkali metal carboxylates or alkaline earth metal carboxylates or a mixture thereof and the catalytically active metals in the form of their reaction products from an aldehyde oxidation reaction. It has surprisingly been found that a catalyst system which is used in the form of its reaction product from an aldehyde oxidation gives a significant increase in conversion into the desired carboxylic acid at high selectivity in the aldehyde oxidation, so that overall higher yields of the desired carboxylic acids are achieved compared to a process in which a fresh catalyst system prepared from metals, preferably in finely divided form, or from commercially available metal salts, for example from acetates, acetylacetonates, metal carbonyls, carbonates, halides, sulfates or metal oxides is employed.

The preparation of the catalyst system in the form of its reaction product is carried out in a separate aldehyde oxidation reaction in which the aldehyde which is oxidized is preferably that which also serves as starting material in the actual oxidation step. The preparation of this reaction product and the actual oxidation reaction are likewise preferably carried out under identical reaction conditions, although the use of different aldehydes and the setting of different reaction conditions in the preparation of the reaction product and the separate actual oxidation reaction are not ruled out.

After the separate reaction of the metals used in the aldehyde oxidation reaction, which can also be referred to as preforming or activation of the catalyst system, the carboxylic acids formed, unreacted starting aldehyde and further volatile constituents are distilled off from the reaction mixture and the distillation residue containing the reaction product is used for the subsequent, actual aldehyde oxidation reaction.

The catalyst-containing residue obtained in the work-up by distillation of the crude carboxylic acid mixture from the subsequent, actual aldehyde oxidation reaction can subsequently be reused as catalyst for the next aldehyde oxidation reaction. Particular purification of the catalyst system for reuse is not necessary. The catalyst system present in the distillation residue of the actual oxidation reaction can thus also be considered to be a reaction product from the aldehyde oxidation reaction.

In the preparation of the reaction product from the aldehyde oxidation reaction, the amounts of alkali metal carboxylates or alkaline earth metal carboxylates, calculated as alkali or alkaline earth metal, used per mol of aldehyde are from 0.5 mmol to 5 mmol.

The total amount of alkali metal carboxylates or alkaline earth metal carboxylates added, including carboxylates in the form of their mixtures, should not exceed a maximum total value of 5 mmol of alkali and/or alkaline earth metal, based on 1 mol of aldehyde.

Particularly high yields are achieved when from 1 mmol to 5 mmol and in particular from 1 mmol to 3 mmol of alkali metal carboxylate or alkaline earth metal carboxylate, calculated as alkali or alkaline earth metal, is added per mol of aldehyde.

It is not necessary for the alkali metal carboxylates or alkaline earth metal carboxylates to be used as a uniform compound. It is likewise possible to use mixtures of these compounds and also mixtures of alkali metal carboxylates and alkaline earth metal carboxylates, but it is advantageous to use the carboxylates of the carboxylic acids formed in the oxidation. However, preference is given to using uniform compounds, for example lithium, potassium, sodium, magnesium, calcium or barium carboxylates, e.g. potassium isononanoate, sodium isononanoate, calcium isononanoate, barium isononanoate, potassium pentanoate, sodium pentanoate, calcium pentanoate or barium pentanoate.

In general, a solution comprising alkali metal carboxylate or alkaline earth metal carboxylate is prepared by neutralizing an aqueous solution comprising the alkali metal compound or alkaline earth metal compound with an excess of the particular desired carboxylic acid and this solution is added to the aldehyde to be oxidized in the preparation of the reaction product from the aldehyde oxidation reaction. Suitable alkali metal or alkaline earth metal compounds are, in particular, the hydroxides, carbonates or hydrogencarbonates.

However, it is also possible to generate the alkali metal carboxylates or alkaline earth metal carboxylates in the reaction mixture by adding alkali metal or alkaline earth metal compounds which are converted into the carboxylates under the reaction conditions to the reaction mixture. For example, alkali metal or alkaline earth metal hydroxides, carbonates, hydrogencarbonates or oxides can be used in the process of the invention. They can be added either in solid form or as an aqueous solution.

In the preparation of the reaction product from the aldehyde oxidation reaction, according to the invention, at least one metal from groups 4 to 12 of the Periodic Table of the Elements (version in accordance with the IUPAC recommendation of 1985), cerium or lanthanum or at least one compound of such a metal is/are added to the oxidation mixture in addition to the alkali metal carboxylate or alkaline earth metal carboxylate. If metals in elemental form are used as catalysts, it is advisable to add them in finely divided form to the reaction mixture. Instead of metals in elemental form, it is also possible to employ compounds of the metals as catalysts. The type of compounds is not subject to any restriction. However, unless there are particular reasons, preference will be given to compounds which are soluble from the beginning in the reaction mixture so as to avoid a delay in commencement of the reaction due to prior formation of a soluble and thus particularly active metal compound.

Metals of groups 4 to 12 which are catalytically active even in a very small amount include titanium, vanadium, chromium, molybdenum, iron, cobalt, nickel, ruthenium, rhodium, palladium, copper, zinc, preferably chromium, titanium, iron, copper, zinc and in particular titanium, iron and chromium. Cerium and lanthanum have likewise been found to be suitable as active metals. As compounds which are soluble in the reaction mixture, use is made of salts, in particular salts of organic acids, preferably carboxylates of the acids which are the result of the separate, actual aldehyde oxidation reaction. Other suitable compounds of the metals used according to the invention are complexes, e.g. acetylacetonates, metal carbonyls or commercially available metal salts such as acetates, carbonates, halides, sulfates or metal oxides or metal alkoxides.

For the preparation of the reaction product from the aldehyde oxidation reaction, it is not necessary to use the catalytically active metals or the compounds containing catalytically active metals as pure substances. Instead, it is also possible to use mixtures of the metals mentioned or the metal compounds and likewise mixtures of metals and metal compounds for the preparation of the preformed catalyst system.

A maximum weight ratio of metal to aldehyde to be oxidized is to be adhered to in the preparation of the reaction product from the aldehyde oxidation reaction. According to the invention, the upper limit to this ratio is 5 ppm, i.e. 5 parts by weight of catalyst metal per $10^6$ parts by weight of aldehyde. It has been found to be particularly useful to employ from 0.1 to 3 parts by weight of catalyst metal, preferably from 0.1 to 2 parts by weight of catalyst metal, per $10^6$ parts by weight of aldehyde. The above-described ratios of catalyst metal to aldehyde also apply when using metal compounds, i.e. the amount of the compound to be used is calculated according to its metal content. An analogous situation applies to the use of mixtures of various catalytically active metals or metal compounds and of mixtures of metals and metal compounds.

The preparation of the reaction product from the aldehyde oxidation reaction is carried out in a temperature range from 20 to 100° C. It is preferably carried out at from 20 to 80° C., in particular from 40 to 80° C. The temperature conditions, viz. constant or variable temperature, can be matched to the individual requirements of the starting material and the circumstances of the reaction.

The reactants are preferably reacted at atmospheric pressure. However, the use of superatmospheric pressure is not ruled out. The reaction is usually carried out in a range from atmospheric pressure to 1.0 MPa, preferably from atmospheric pressure to 0.8 MPa.

The reaction time required for the preparation of the reaction product from the aldehyde oxidation reaction depends, inter alia, on the reaction temperature, the type of starting materials and the ratio of the reactants to one another. It is normally from 30 minutes to 20 hours, in particular from 2 to 8 hours.

The reaction mixture is subsequently distilled and the desired carboxylic acid already obtained is separated off. Residual amounts of aldehyde which have likewise been separated off by distillation can be reused in the actual, separate aldehyde oxidation reaction. The distillation is generally continued to such an extent that the distillation residue obtained, which contains the reaction product from the aldehyde oxidation reaction, i.e. the activated catalyst system, in solution, is still able to be handled industrially, for example is still sufficiently pumpable.

The reaction product from the aldehyde oxidation reaction present in the distillation residue is subsequently added to the aldehyde to be oxidized in the actual oxidation reaction, which is preferably the same aldehyde as that used in the preparation of the reaction product from the aldehyde oxidation reaction.

The amounts of metal employed and the weight ratios of metal to aldehyde to be oxidized correspond to the amounts and ratios employed in the preparation of the reaction product from the aldehyde oxidation reaction.

In a further embodiment of the process of the invention, it is also possible for alkali metals or alkaline earth metals and catalytically active metals of groups 4 to 12 of the Periodic Table of the Elements and cerium or lanthanum to be employed in the preparation of the reaction product from the aldehyde oxidation reaction in amounts which are up to five times, preferably up to three times, the amount of metal required in the case of direct use of the reaction product from the aldehyde oxidation reaction for the subsequent actual aldehyde oxidation reaction. In this embodiment of the process of the invention, the distillation residue obtained after the carboxylic acids formed, the unreacted residual aldehyde and further volatile constituents have been separated off by distillation is not used in its entirety for the subsequent, actual aldehyde oxidation reaction but rather in such an amount that the metal content in the aldehyde to be oxidized is in the range set when the reaction product from the aldehyde oxidation reaction is used directly for the subsequent, actual aldehyde oxidation reaction.

The present invention therefore likewise provides a catalytic process for preparing aliphatic straight-chain and β-alkyl-branched carboxylic acids having from 5 to 13 carbon atoms by oxidation of the corresponding aldehydes by means of oxygen or oxygen-containing gas mixtures at from 20 to 100° C. in the liquid phase, wherein the oxidation of the aldehydes is carried out in the presence of a catalyst system which is the reaction product from an aldehyde oxidation reaction in which the aldehyde oxidation reaction is carried out in the presence of alkali metal carboxylates or alkaline earth metal carboxylates or a mixture thereof in an amount, calculated as alkali or alkaline earth metal of, from 2.5 mmol to 25 mmol per mol of aldehyde used and from 0.25 to 25 ppm of a metal of groups 4 to 12 of the Periodic Table of the Elements, cerium or lanthanum or the corresponding amount of a compound of such a metal or a mixture of such metals and/or metal compounds, based on the aldehyde used, and is used for the oxidation of the aldehydes in such an amount that the oxidation of the aldehydes is carried out in the presence of alkali metal carboxylates or alkaline earth metal carboxylates or a mixture thereof in an amount, calculated as alkali or alkaline earth metal, of from 0.5 mmol to 5 mmol per mol of aldehyde used and of from 0.05 to 5.0 ppm of a metal of groups 4 to 12 of the Periodic Table of the Elements, cerium or lanthanum or the corresponding amount of a compound of such a metal or a mixture of such metals and/or metal compounds, based on the aldehyde used.

The amounts of alkali metal carboxylates or alkaline earth metal carboxylates used, calculated as alkali or alkaline earth metal, are preferably from 1.5 mmol to 15 mmol per mol of aldehyde used in the preparation of the reaction product from the aldehyde oxidation reaction. The catalytically active metals of groups 4 to 12 of the Periodic Table of the Elements, cerium or lanthanum are preferably present in an amount of from 0.15 to 15 ppm, based on the aldehyde used.

After the catalyst has been preformed and carboxylic acid, residual aldehyde and volatile components have been separated off by distillation, part of the distillation residue obtained is used for the actual aldehyde oxidation reaction. The amount of the distillation residue used is such that the amounts of alkali metal carboxylates or alkaline earth metal carboxylates and of transition metals of groups 4 to 12 of the Periodic Table of the Elements, cerium or lanthanum present, based on the aldehyde to be oxidized, correspond to the amounts and preferred amounts used when the reaction product from the aldehyde oxidation reaction is used directly for the subsequent, actual aldehyde oxidation reaction.

The amounts of metal employed ensure a reaction rate sufficient for industrial requirements. However, they do not give rise to undesirable secondary reactions, so that the aldehydes are converted virtually exclusively into the corresponding carboxylic acids. In addition, the amounts of metal used are so small that they do not have to be recovered or removed from the reaction product either from the point of view of the economics of the process, e.g. when using expensive noble metals, or with a view to the purity of the carboxylic acids required for various fields of application.

The temperature and pressure ranges selected in the actual, subsequent aldehyde oxidation reaction also correspond to the conditions employed in the preparation of the reaction products from the aldehyde oxidation reaction.

Thus, the oxidation of aliphatic straight-chain and β-alkyl-branched aldehydes having from 5 to 13 carbon atoms is preferably carried out at temperatures in the range from 20 to 80° C., in particular from 40 to 80° C., and at pressures in the range from atmospheric pressure to 1.0 MPa, preferably at from atmospheric pressure to 0.8 MPa.

The reaction time required in the oxidation reaction depends, inter alia, on the reaction temperature, the type of starting materials and the ratio of the reactants to one another. It is normally from 30 minutes to 20 hours, in particular from 2 to 8 hours.

In the preparation of the reaction product from the aldehyde oxidation reaction and in the actual, separate aldehyde oxidation reaction, molecular oxygen or gas mixtures comprising molecular oxygen are used as oxidant. Further constituents of such gas mixtures are inert gases, e.g. nitrogen, noble gases and carbon dioxide. The proportion of inert constituents of the oxygen-containing gas mixture is up to 90% by volume, in particular from 30 to 80% by volume. Preferred oxidants are oxygen and air.

The aldehydes can be used as such or as a solution in a solvent which is inert under the reaction conditions. Examples of suitable solvents are ketones such as acetone, esters, e.g. ethyl acetate, hydrocarbons, e.g. toluene, and nitrohydrocarbons such as nitrobenzene. The concentration of the aldehyde is limited by its solubility in the solvent.

Both the preforming step for the catalyst system and the actual aldehyde oxidation reaction can be carried out batchwise or continuously. Recirculation of unreacted reaction participants is possible in both cases.

The pure carboxylic acid is isolated from the crude acid mixture obtained after the oxidation by means of distillation under customary conditions. The distillation residue comprising the alkali metal carboxylates or alkaline earth metal carboxylates and catalytic metals is separated off and can be added again to the starting aldehyde, if appropriate after addition of fresh alkali metal carboxylates or alkaline earth metal carboxylates or alkali metal compounds or alkaline earth metal compounds which are converted into the carboxylates under the reaction conditions and also of catalytically active metals.

In a useful embodiment of the process of the invention, the aldehyde together with the alkali metal carboxylates or alkaline earth metal carboxylates and the catalytic metal are placed in a suitable reactor, e.g. a tube reactor which is provided with an inflow plate and may also contain packing, and the oxygen or the oxygen-containing gas mixture is passed from below through the aldehyde. The preforming step for the catalyst system is carried out analogously.

In a further embodiment, a trickle tower containing packing is used as reactor. The aldehyde containing alkali metal carboxylates or alkaline earth metal carboxylates and catalytic metal is allowed to trickle down over the packing and oxygen or an oxygen-containing gas mixture is simultaneously introduced into the tower in cocurrent or countercurrent.

The oxidation of aliphatic straight-chain or β-alkyl-branched aldehydes having from 5 to 13 carbon atoms is at the center of the novel process. For the purposes of the present invention, β-alkyl-branched aldehydes include aldehydes which bear further side groups on the carbon skeleton in addition to the β-alkyl branch. The origin of the aldehydes is not restricted to particular preparative processes. Owing to their ready availability, aldehydes obtained by means of the oxo process, i.e. by reaction of olefins having from 4 to 12 carbon atoms with carbon monoxide and hydrogen, are preferred. In this context, it is not critical which particular embodiment of the oxo process has been employed for obtaining the aldehydes, i.e. whether the reaction has been catalyzed by, for example, cobalt or rhodium, whether the metals were used alone or together with complexing agents and the catalyst was homogeneously dissolved in the reaction mixture or formed a separate, heterogeneous phase.

The process of the invention is particularly useful for preparing isononanoic acid from the reaction product of the oxo process carried out using diisobutylene. The industrially available reaction product of the hydroformylation of diisobutylene comprises 3,5,5-trimethylhexanal as main constituent together with small amounts of 3,4,4- and 3,4,5-trimethylhexanal. In addition, small amounts of aldehydes which are not branched in the β-position, e.g. 2,5,5-trimethylhexanal, 4,5,5-trimethylhexanal and 6,6-dimethylheptanal, are present. The oxidation of this industrially available mixture of isomeric nonanals by the process of the invention leads to a considerable increase in conversion together with an outstanding selective formation of isononanoic acid.

The process of the invention is likewise very suitable for the oxidation of n-pentanal, n-heptanal, n-nonanal and isovaleraldehyde to the corresponding carboxylic acids.

The following examples describe the preparation of n-pentanoic acid and isononanoic acid by the process claimed.

The preparation of the reaction product from the aldehyde oxidation reaction is carried out in accordance with the invention in the presence of alkali metal carboxylates or alkaline earth metal carboxylates and of the catalytic metals by oxygen oxidation of the aldehyde to be oxidized. After volatile components have been separated off by distillation, the precipitated distillation residue is used as catalyst system for the subsequent aldehyde oxidation reaction. The catalyst residue obtained after the actual aldehyde oxidation reaction is reused for subsequent aldehyde oxidation reactions.

The respective experimental results are reported by way of the following parameters:
aldehyde conversion;
selectivity, calculated from the proportion of carboxylic acid in the reaction product, based on aldehyde reacted;
yield of carboxylic acid.

Of course, the novel process is not restricted to the embodiment described below.

EXAMPLES

1. Direct Use of the Reaction Product from the Aldehyde Oxidation Reaction for the Aldehyde Oxidation Reaction
Procedure:

The liquid-phase oxidation of aldehyde to carboxylic acid was carried out in a bubble column reactor made of glass which had an internal diameter of 38 mm and a length of 150 cm. Depending on the reaction behavior, the reactor was cooled or heated via its wall by means of a water circuit connected to a heat exchanger and the internal temperature was kept constant in this way. The oxygen was fed in from below through a glass filter plate which was joined to the bubble column and had a maximum pore width of 16-40 μm.

After the reaction was complete, the crude acid was all distilled in a simple vacuum distillation apparatus at a pressure of 100 hPa, the residue which remained was mixed with fresh aldehyde and the solution obtained in this way was subsequently oxidized.

Preparation of the Reaction Product from the Aldehyde Oxidation Reaction (Use of Fresh Catalyst), Catalyst Preforming The starting material for the oxidation comprised a mixture of
a) 760.0 g of aldehyde
b) a homogeneous solution of alkali metal carboxylate or alkaline earth metal carboxylate in carboxylic acid, prepared by dissolving alkali metal hydroxide or alkaline earth metal hydroxide in carboxylic acid in a molar ratio of 1:4
c) a metal-containing acid; the acid concerned likewise the respective target product
d) a particular amount of pure carboxylic acid; likewise the respective target product Instead of the, solutions b) and c), it is also possible to use a solution b) which is admixed directly with a suitable metal compound. The amounts of carboxylic acid used in items b)-d) corresponded essentially to a total value of 40.0 g. Detailed information may be found in the individual examples.

Actual Aldehyde Oxidation Reaction; Reuse of Catalyst

The starting material for the actual aldehyde oxidation reaction comprised a mixture of
a) 760.0 g of aldehyde
b) the distillation residue (generally less than 40 g) from the preparation of the reaction product from the aldehyde oxidation reaction or the preceding aldehyde oxidation reaction in the case of reuse of catalyst
c) a particular amount of pure carboxylic acid, likewise the respective target product The amounts of carboxylic acid used under items b) and c) corresponded essentially to a total value of 40.0 g. Detailed information may be found in the individual examples.

Evaluation of the Experiment:

The values reported in the GC analyses are percent by area and in the case of carboxylic acid also include the amount already in use in each case. Since the amounts of aldehyde and carboxylic acid used were always kept constant at 760.0 g and 40.0 g, respectively, comparison of the GC analyses within a series of experiments is permissible.

In the case of the figures given for conversion, selectivity and yield, the amount of carboxylic acid used has been taken out of the calculation, so that these figures relate only to the result of the oxidation, namely the respective aldehyde conversion and the amount of carboxylic acid formed as a result.

Example 1

Preparation of n-pentanoic Acid

The aldehyde used in the oxidation had the following composition:
GC analysis: 0.06% of fore-run components
  0.64% of isopentanal
  99.15% of n-pentanal
  0.10% of n-pentanoic acid
  0.05% of other components a) Preparation of the Reaction Product from the Aldehyde Oxidation Reaction; Use of Fresh Catalyst (Combination Iron/Potassium)

The starting batch for the oxidation comprised a homogeneous mixture of 760.0 g of n-pentanal, 37.3 g of n-pentanoic acid having a content of 1.52 mg of iron (introduced as iron (II) acetate) and 4.59 g of a solution comprising, 1.24 g of potassium n-pentanoate, 2.70 g of n-pentanoic acid and 0.65 g of water.

After oxidation at a constant 50° C. for 2.5 hours and a total consumption of 106 liters of oxygen (measured at 20° C.), a crude acid having the following composition was obtained:
GC analysis: 0.11% of fore-run components
  0.07% of isopentanal
  11.34% of n-pentanal
  0.26% of components
  0.55% of isopentanoic acid
  87.26% of n-pentanoic acid
  0.41% of after-run components The conversion (based on n-pentanal) was 86.1% of theory, and the associated selectivity to formation of n-pentanoic acid was 98.8% of theory. A yield of 85.1% can be calculated therefrom.

b) Actual Aldehyde Oxidation Reaction; Reuse of Catalyst

The catalyst system preformed in the above-described experiment was recirculated a total of four times in the form of the residue of the distillation of the acid to the oxidation. In the 4th reuse of the catalyst, the starting batch for the oxidation comprised a homogeneous mixture of 760.0 g of n-pentanal, 38.9 g of distillation residue (1.2 g of potassium n-pentanoate present therein) and 2.3 g of n-pentanoic acid.

The oxidation was carried out under the abovementioned conditions as in the preforming of the catalyst (reaction time: 2.5, hours, reaction temperature: 50° C., 106 liters of oxygen (measured at 20° C.)). A crude acid having the following composition was obtained:
  0.16% of fore-run components
  0.03% of isopentanal
  5.33% of n-pentanal
  0.37% of components
  0.57% of isopentanoic acid
  92.92% of n-pentanoic acid
  0.62% of after-run components As a result of the cycling of the catalyst, the aldehyde conversion of 86.1% when using fresh catalyst increased to 93.4% in the 4th reuse of the catalyst, and the yield improved from 85.1% to 92.3% in these experiments.

Example 2

Preparation of Isononanoic Acid

Starting aldehyde GC analysis: 1.55% of fore-run components
  96.55% of isononanal
  1.34% of isononanols
  0.07% of isononanoic acid
  0.49% of other components a) Preparation of the Reaction Product from the Aldehyde Oxidation Reaction; Use of Fresh Catalyst (Combination Iron/Potassium)

The starting batch for the oxidation comprised a homogeneous mixture of 760.0 g of isononanal, 34.9 g of isononanoic acid having a content of 0.76 mg of iron and 7.96 g of a solution comprising 2.10 g of potassium isononanoate, 5.07 g of isononanoic acid and 0.79 g of water.

After oxidation at a constant 60° C. for 2 hours and a total consumption of 64.4 liters of oxygen (measured at 20° C.), a crude acid having the following composition was obtained:
  1.76% of fore-run components
  10.07% of isononanal
  1.22% of isononanols
  85.55% of isononanoic acid
  1.40% of other components The conversion (based on isononanal) was 88.0% of theory, and the associated selectivity to formation of isononanoic acid was 97.8% of theory. A yield of 86.1% can be calculated therefrom.

b) Actual Aldehyde Oxidation Reaction; Reuse of the Catalyst

The catalyst system preformed in the above-described experiment was recirculated a total of three times in the form of the residue from the distillation of the acid to the oxidation. In the 3rd reuse of the catalyst, the starting batch for the oxidation comprised a homogeneous mixture of 760.0 g of isononanal, 36.9 g of distillation residue (2.1 g of potassium isononanoate present therein) and 5.2 g of isononanoic acid.

The oxidation was carried out under the abovementioned conditions as in the preforming of the catalyst (reaction time: 2 hours, reaction temperature: 60° C., 64.4 liters of oxygen (measured at 20° C.)). A crude acid having the following composition was obtained:
  2.03% of fore-run components
  3.18% of isononanal
  1.22% of isononanols
  91.30% of isononanoic acid
  2.27% of other components As a result of the cycling of the catalyst, the aldehyde conversion increased from 88.0% when fresh catalyst was used to 96.2% in the 3rd use of the catalyst, and the yield improved from 86.1% to 92.2% in these experiments.

Example 3

Preparation of n-pentanoic Acid

Starting aldehyde GC analysis: 0.06% of fore-run components
  0.64% of isopentanal
  99.15% of n-pentanal
  0.10% of n-pentanoic acid
  0.05% of other components a) Preparation of the Reaction Product from the Aldehyde Oxidation Reaction; Use of Fresh Catalyst (Combination Copper/Potassium)

The starting batch for the oxidation comprised a homogeneous mixture of 760.0 g of n-pentanal, 37.3 g of n-pentanoic acid having a content of 0.76 mg of copper and 4.59 g of a solution comprising 1.24 g of potassium n-pentanoate, 2.70 g of n-pentanoic acid and 0.65 g of water.

After oxidation at a constant 50° C. for 2.5 hours and a total consumption of 106 liters of oxygen (measured at 20° C.), a crude acid having the following composition was obtained:

0.17% of fore-run components
0.05% of isopentanal
8.57% of n-pentanal
0.28% of components.
0.55% of isopentanoic acid
90.26% of n-pentanoic acid
0.12% of after-run components The conversion (based on n-pentanal) was 89.5% of theory, and the associated selectivity to formation of n-pentanoic acid was 98.7% of theory. A yield of 88.3% can be calculated therefrom.

b) Actual Aldehyde Oxidation Reaction; Reuse of the Catalyst

The catalyst system preformed in the above-described experiment was recirculated a total of two times in the form of the residue of the distillation of the acid to the oxidation. In the 2nd reuse of the catalyst, the starting batch for the oxidation comprised a homogeneous mixture of 760.0 g of n-pentanal, 37.3 g of distillation residue (1.2 g of potassium n-pentanoate present therein) and 3.9 g of n-pentanoic acid.

The oxidation was carried out under the abovementioned conditions as in the preforming of the catalyst (reaction time: 2.5 hours, reaction temperature: 50° C., 106 liters of oxygen (measured at 20° C.)). A crude acid having the following composition was obtained:
0.25% of fore-run components
0.01% of isopentanal
2.10% of n-pentanal
0.32% of components
0.59% of isopentanoic acid
96.44% of n-pentanoic acid
0.29% of after-run components As a result of the cycling of the catalyst, the aldehyde conversion increased from 89.5% when fresh catalyst was used to 97.4% in the 2nd reuse of the catalyst, and the yield improved from 88.3% to 95.8% in these experiments.

Example 4

Preparation of n-pentanoic Acid

Starting aldehyde GC analysis: 0.05% of fore-run components
0.36% of isopentanal
99.46% of n-pentanal
0.09% of n-pentanoic acid
0.04% of other components a) Preparation of the Reaction Product from the Aldehyde Oxidation Reaction; Use of Fresh Catalyst (Combination Chromium/Potassium)

The starting batch for the oxidation comprised a homogeneous mixture of 760.0 g of n-pentanal, 37.3 g of n-pentanoic acid having a content of 0.76 mg of chromium and 4.59 g of a solution comprising 1.24 g of potassium n-pentanoate, 2.70 g of n-pentanoic acid and 0.65 g of water.

After oxidation at a constant 50° C. for 2.5 hours and a total consumption of 106 liters of oxygen (measured at 20° C.), a crude acid having the following composition was obtained:
0.20% of fore-run components
0.04% of isopentanal
6.64% of n-pentanal
0.39% of components
0.56% of isopentanoic acid
91.77% of n-pentanoic acid
0.40% of after-run components The conversion (based on n-pentanal) was 91.8% of theory, and the associated selectivity to formation of n-pentanoic acid was 98.3% of theory. A yield of 90.3% can be calculated therefrom.

b) Actual Aldehyde Oxidation Reaction; Reuse of the Catalyst

The catalyst system preformed in the above-described experiment was recirculated a total of two times in the form of the residue of the distillation of the acid to the oxidation. In the 2nd reuse of the catalyst, the starting batch for the oxidation comprised a homogeneous mixture of 760.0 g of n-pentanal, 36.2 g of distillation residue (1.2 g of potassium n-pentanoate present therein) and 4.9 g of n-pentanoic acid.

The oxidation was carried out under the abovementioned conditions as in the preforming (reaction time: 2.5 hours, reaction temperature: 50° C., 106 liters of oxygen (measured at 20° C.)). A crude acid having the following composition was obtained:
0.47% of fore-run components
0.01% of isopentanal
1.43% of n-pentanal
0.57% of components
0.58% of isopentanoic acid
96.41% of n-pentanoic acid
0.53% of after-run components As a result of the cycling of the catalyst, the aldehyde conversion increased from 91.8% when fresh catalyst was used to 98.2% in the 2nd reuse of the catalyst, and the yield improved from 90.3% to 95.9% in these experiments.

Example 5

Preparation of n-pentanoic Acid

Starting aldehyde GC analysis: 0.06% of fore-run components
0.64% of isopentanal
99.15% of n-pentanal
0.10% of n-pentanoic acid
0.05% of other components a) Preparation of the Reaction Product from the Aldehyde Oxidation Reaction; Use of Fresh Catalyst (Combination Iron/barium)

The starting batch for the oxidation comprised a homogeneous mixture of 760.0 g of n-pentanal, 27.4 g of n-pentanoic acid having a content of 1.52 mg of iron and 17.21 g of a solution comprising 3.00 g of barium n-pentanoate, 12.62 g of n-pentanoic acid and 1.59 g of water.

After oxidation at a constant 50° C. for 2.5 hours and a total consumption of 106 liters of oxygen (measured at 20° C.), a crude acid having the following composition was obtained:
0.16% of fore-run components
0.08% of isopentanal
12.00% of n-pentanal
0.18% of components
0.55% of isopentanoic acid
86.76% of n-pentanoic acid
0.27% of after-run components The conversion (based on n-pentanal) was 85.3% of theory, and the associated selectivity to formation of n-pentanoic acid was 99.1% of theory. A yield of 84.5% can be calculated therefrom.

b) Actual Aldehyde Oxidation Reaction; Reuse of the Catalyst

The catalyst system preformed in the above-described experiment was recirculated a total of two times in the form of the residue from the distillation of the acid to the oxidation. In the 2nd reuse of the catalyst, the starting batch for the oxidation comprised a homogeneous mixture of 760.0 g of n-pentanal, 42.5 g of distillation residue (3.0 g of barium n-pentanoate present therein) and 0.5 g of n-pentanoic acid.

The oxidation was carried out under the abovementioned conditions as in the preforming (reaction time: 2.5 hours, reaction temperature: 50° C., 106 liters of oxygen (measured at 20° C.)). A crude acid having the following composition was obtained:

0.16% of fore-run comporments
0.04% of isopentanal
5.31% of n-pentanal
0.17% of components
0.58% of isopentanoic acid
93.23% of n-pentanoic acid
0.51% of after-run components As a result of the cycling of the catalyst, the aldehyde conversion increased from 85.3% when fresh catalyst was used to 93.4% in the 2nd reuse of the catalyst, and the yield improved from 84.5% to 92.5% in these experiments.

Example 6

Preparation of n-pentanoic Acid

Starting aldehyde GC analysis: 0.06% of fore-run components
0.64% of isopentanal
99.15% of n-pentanal
0.10% of n-pentanoic acid
0.05% of other components a) Preparation of the Reaction Product from the Aldehyde Oxidation Reaction; Use of Fresh Catalyst (Combination Iron/Sodium)

The starting batch for the oxidation comprised a homogeneous mixture of 760.0 g of n-pentanal, 37.3 g of n-pentanoic acid having a content of 1.52 mg of iron and 4.31 g of a solution comprising 1.10 g of sodium n-pentanoate, 2.70 g of n-pentanoic acid and 0.51 g of water.

After oxidation at a constant 50° C. for 2.5 hours and a total consumption of 106 liters of oxygen (measured at 20° C.), a crude acid having the following composition was obtained:

0.13% of fore-run components
0.06% of isopentanal
10.62% of n-pentanal
0.32% of components
0.51% of isopentanoic acid
88.18% of n-pentanoic acid
0.18% of after-run components The conversion (based on n-pentanal) was 87.0% of theory, and the associated selectivity to formation of n-pentanoic acid was 99.1% of theory. A yield of 86.2% can be calculated therefrom.

b) Actual Aldehyde Oxidation Reaction; Reuse of the Catalyst

The catalyst system preformed in the above-described experiment was recirculated a total of two times in the form of the residue from the distillation of the acid to the oxidation. In the 2nd reuse of the catalyst, the starting batch for the oxidation comprised a homogeneous mixture of 760.0 g of n-pentanal, 30.4 g of distillation residue (1.1 g of sodium n-pentanoate present therein) and 10.8 g of n-pentanoic acid.

The oxidation was carried out under the abovementioned conditions as in the preforming (reaction time: 2.5 hours, reaction temperature: 50° C., 106 liters of oxygen (measured at 20° C.)). A crude acid having the following composition was obtained:

0.14% of fore-run components
0.03% of isopentanal
5.33% of n-pentanal
0.35% of components
0.57% of isopbntanoic acid
93.27% of n-pentanoic acid
0.31% of after-run components As a result of the cycling of the catalyst, the aldehyde conversion increased from 87.0% when fresh catalyst was used to 93.4% in the 2nd reuse of the catalyst, and the yield improved from 86.2% to 92.1% in these experiments.

Example 7

Preparation of n-pentanoic Acid

Starting aldehyde GC analysis: 0.06% of fore-run components
0.64% of isopentanal
99.15% of n-pentanal
0.10% of n-pentanoic acid
0.05% of other components a) Preparation of the Reaction Product from the Aldehyde Oxidation Reaction; Use of Fresh Catalyst (Combination Zinc/Potassium)

The starting batch for the oxidation comprised a homogeneous mixture of 760.0 g of n-pentanal, 37.3 g of n-pentanoic acid having a content of 0.76 mg of zinc and 4.59 g of a solution comprising 1.24 g of potassium n-pentanoate, 2.70 g of n-pentanoic acid and 0.65 g of water.

After oxidation at a constant 50° C. for 2.5 hours and a total consumption of 106 liters of oxygen (measured at 20° C.), a crude acid having the following composition was obtained:

0.15% of fore-run components
0.07% of isopentanal
11.44% of n-pentanal
0.25% of components
0.55% of isopentanoic acid
87.34% of n-pentanoic acid
0.20% of after-run components The conversion (based on n-pentanal) was 86.0% of theory, and the associated selectivity to formation of n-pentanoic acid was 99.0% of theory. A yield of 85.1% can be calculated therefrom.

b) Actual Aldehyde Oxidation Reaction; Reuse of the Catalyst

The catalyst system preformed in the above-described experiment was recirculated a total of two times in the form of the residue from the distillation of the acid to the oxidation. In the 2nd reuse of the catalyst, the starting batch for the oxidation comprised a homogeneous mixture of 760.0 g of n-pentanal, 36.5 g of distillation residue (1.2 g of potassium n-pentanoate present therein) and 4.7 g of n-pentanoic acid.

The oxidation was carried out under the abovementioned conditions as in the preforming (reaction time: 2.5 hours, reaction temperature: 50° C., 106 liters of oxygen (measured at 20° C.)). A crude acid having the following composition was obtained:

0.18% of fore-run components
0.02% of isopentanal
3.43% of n-pentanal
0.38% of components
0.58% of isopentanoic acid
95.08% of n-pentanoic acid
0.33% of after-run components As a result of the cycling of the catalyst, the aldehyde conversion increased from 86.0% when fresh catalyst was used to 95.7% in the 2nd reuse of the catalyst, and the yield improved from 85.1% to 94.5% in these experiments.

Example 8

Preparation of n-pentanoic Acid

Starting aldehyde GC analysis: 0.06% of fore-run components
  0.64% of isopentanal
  99.15% of n-pentanal
  0.10% of n-pentanoic acid
  0.05% of other components
  a) Preparation of the Reaction Product from the Aldehyde Oxidation Reaction; Use of Fresh Catalyst (Combination Iron/Potassium)

The starting batch for the oxidation comprised a homogeneous mixture of 760.0 g of n-pentanal, 37.3 g of n-pentanoic acid having a content of 1.52 mg of iron (introduced as iron (II) acetate) and 4.59 g of a solution comprising 1.24 g of potassium n-pentanoate, 2.70 g of n-pentanoic acid and 0.65 g of water.

After oxidation at a constant 50° C. for 3 hours and a total consumption of 112 liters of oxygen (measured at 20° C.), a crude acid having the following composition was obtained:
  0.11% of fore-run components
  0.05% of isopentanal
  8.21% of n-pentanal
  0.26% of components
  0.57% of isopentanoic acid
  90.46% of n-pentanoic acid
  0.34% of after-run components The conversion (based on n-pentanal) was 89.9% of theory, and the associated selectivity to formation of n-pentanoic acid was 98.9% of theory. A yield of 88.9% can be calculated therefrom.

b) Actual Aldehyde Oxidation Reaction; Reuse of the Catalyst

The catalyst system preformed in the above-described experiment was recirculated a total of four times in the form of the residue from the distillation of the acid to the oxidation. In the 4th reuse of the catalyst, the starting batch for the oxidation comprised a homogeneous mixture of 760.0 g of n-pentanal, 38.9 g of distillation residue (1.2 g of potassium n-pentanoate present therein) and 2.3 g of n-pentanoic acid.

The oxidation was carried out under the abovementioned conditions as in the preforming (reaction time: 3 hours, reaction temperature: 50° C., 112 liters of oxygen (measured at 20° C.)). A crude acid having the following composition was obtained:
  0.16% of fore-run components
  0.02% of isopentanal
  3.35% of n-pentanal
  0.38% of components
  0.58% of isopentanoic acid
  94.94% of n-pentanoic acid
  0.57% of after-run components As a result of the cycling of the catalyst, the aldehyde conversion increased from 89.9% when fresh catalyst was used to 95.8% in the 4th reuse of the catalyst, and the yield improved from 88.9% to 94.4% in these experiments.

The metals and amounts of metals used in examples 1 to 8 are summarized in table 1 below. As the results of the examples demonstrate, the aldehyde conversion can be improved significantly at a high aldehyde selectivity when the catalyst system is used in the form of its reaction product from the aldehyde oxidation reaction. In contrast, the use of fresh catalyst gives lower conversions throughout in the aldehyde oxidation reaction.

TABLE 1

Oxidation of n-pentanal and isononanal to the corresponding carboxylic acid using a catalyst system containing a mixture of alkali or alkaline earth metal and transition metal

| Example | Acid | Metal | Alkali | Reuse | Reaction time |
|---|---|---|---|---|---|
| 1 | n-pentanoic acid | 2 ppm of iron | 1 mmol of potassium | 4th cycle | 2.5 hours |
| 2 | isononanoic acid | 1 ppm of iron | 2 mmol of potassium | 3rd cycle | 2 hours |
| 3 | n-pentanoic acid | 1 ppm of copper | 1 mmol of potassium | 2nd cycle | 2.5 hours |
| 4 | n-pentanoic acid | 1 ppm of chromium | 1 mmol of potassium | 2nd cycle | 2.5 hours |
| 5 | n-pentanoic acid | 1 ppm of iron | 1 mmol of barium | 2nd cycle | 2.5 hours |
| 6 | n-pentanoic acid | 1 ppm of iron | 1 mmol of sodium | 2nd cycle | 2.5 hours |
| 7 | n-pentanoic acid | 1 ppm of zinc | 1 mmol of potassium | 2nd cycle | 2.5 hours |
| 8 | n-pentanoic acid | 2 ppm of iron | 1 mmol of potassium | 4th cycle | 3 hours |

| | Performing of the catalyst [%] | | | Aldehyde oxidation figures after reuse [%] | | |
|---|---|---|---|---|---|---|
| Example | Conversion | Selectivity | Yield | Conversion | Selectivity | Yield |
| 1 | 86.1 | 98.8 | 85.1 | 93.4 | 98.8 | 92.3 |
| 2 | 88.0 | 97.8 | 86.1 | 96.2 | 95.8 | 92.2 |
| 3 | 89.5 | 98.7 | 88.3 | 97.4 | 98.4 | 95.8 |
| 4 | 91.8 | 98.3 | 90.3 | 98.2 | 97.7 | 95.9 |
| 5 | 85.3 | 99.1 | 84.5 | 93.4 | 99.0 | 92.5 |
| 6 | 87.0 | 99.1 | 86.2 | 93.4 | 98.6 | 92.1 |
| 7 | 86.0 | 99.0 | 85.1 | 95.7 | 98.8 | 94.5 |
| 8 | 89.9 | 98.9 | 88.9 | 95.8 | 98.5 | 94.4 |

The amounts reported are based on the aldehyde used.

2. Partial Use of the Reaction Product from the Aldehyde Oxidation Reaction for the Aldehyde Oxidation Reaction The general experimental procedure was as under item 1.

Example 9

Preparation of n-pentanoic Acid

Starting aldehyde GC analysis: 0.06% of fore-run components
  0.64% of isopentanal
  99.15% of n-pentanal
  0.10% of n-pentanoic acid
  0.05% of other components
  a) Preparation of the Reaction Product from the Aldehyde Oxidation Reaction; Use of Fresh Catalyst (Combination Iron/Potassium)

The starting batch for the oxidation comprised a homogeneous mixture of 760.0 g of n-pentanal, 26.5 g of n-pentanoic acid having a content of 3.8 mg of iron (introduced as iron(II) acetate) and 22.95 g of a solution comprising 6.20 g of potassium n-pentanoate, 13.50 g of n-pentanoic acid and 3.25 g of water.

After oxidation at a constant 50° C. for 2.5 hours and a total consumption of 106 liters of oxygen (measured at 20° C.), a crude acid having the following composition was obtained:

0.50% of fore-run components
0.04% of isopentanal
8.66% of n-pentanal
1.20% of components
0.56% of isopentanoic acid
88.08% of n-pentanoic acid
0.96% of after-run components The conversion (based on n-pentanal) was 89.4% of theory, and the associated selectivity to formation of n-pentanoic acid was 96.1% of theory. A yield of 85.9% can be calculated therefrom.

b) Actual Aldehyde Oxidation Reaction; Reuse of the Catalyst

The crude acid prepared in the above-described experiment was distilled, giving an amount of 41.0 g of residue containing the catalyst.

8.2 g of the distillation residue (1.2 g of potassium n-pentanoate present therein) were recirculated together with 760.0 g of n-pentanal and 33.0 g of n-pentanoic acid to the oxidation.

The oxidation was carried out under the abovementioned conditions (reaction time: 2.5 hours, reaction temperature: 50° C., 106 liters of oxygen (measured at 20° C.)). A crude acid having the following composition was obtained:
0.16% of fore-run components
0.03% of isopentanal
5.26% of n-pentanal
0.35% of components
0.57% of isopentanoic acid
93.02% of n-pentanoic acid
0.61% of after-run components The aldehyde conversion was 93.5% and the yield was 92.4%.

A procedure in which the preforming of the catalyst is firstly carried out in the presence of relatively high amounts of metal and part of the catalyst system is subsequently used for the actual, subsequent aldehyde oxidation reaction also leads to a significant increase in the yield of carboxylic acid.

What I claim is:

1. A catalytic process for preparing aliphatic straight-chain and β-alkyl-branched carboxylic acids of 5 to 13 carbon atoms comprising oxidizing the corresponding aldehydes with oxygen or oxygen-containing gas mixtures at 20 to 100° C. in the liquid phase, wherein the oxidation of the aldehyde is carried out in the presence of a catalyst system which is the reaction product from a separate aldehyde oxidation reaction in which the aldehyde oxidation reaction in which the aldehyde oxidation reaction is carried out in the presence of alkali metal carboxylates or alkaline earth metal carboxylates or a mixture thereof in an amount, calculated as alkali or alkaline earth metal, of 0.5 mmol to 5 mmol per mol of aldehyde used and of 0.05 to 5.0 ppm of a metal of groups 4 to 12 of the Periodic Table, cerium or lanthanum or the corresponding amount of a compound of such a metal or a mixture of such metals and metal compounds, based on the aldehyde used, and after said separate aldehyde oxidation reaction, the carboxylic acids formed, unreacted starting aldehyde and further volatile constituents are distilled off from the reaction mixture and the distillation residue containing the reaction product is used for the subsequent, actual aldehyde oxidation reaction.

2. The process of claim 1, wherein the preparation of the reaction product from the separate aldehyde oxidation reaction is carried out in the presence of alkali metal carboxylates or alkaline earth metal or a mixture thereof in an amount, calculated as alkali or alkaline earth metal, of 1 mmol to 5 mmol, per mol of aldehyde used and in the presence of 0.1 to 3 ppm, of a metal of groups 4 to 12 of the Periodic Table, cerium or lanthanum or the corresponding amount of a compound of such a metal or a mixture of such metals and metal compounds, based on the aldehyde used.

3. The process of claim 2 containing 1 mmol to 3 mmol of carboxylate and 0.1 to 2 ppm of metal is used.

4. The process of claim 1, where lithium, sodium or potassium carboxylated are used as alkali metal carboxylates and magnesium, calcium and barium carboxylates are used as alkaline earth metal carboxylates.

5. The process of claim 4, wherein the alkali metal carboxylates or alkaline earth metal carboxylates are salts of the carboxylic acids which are formed as a result of the separate aldehyde oxidation reaction.

6. The process of claim 1, wherein the metal of groups 4 to 12 of the Periodic Table is selected from the group consisting of titanium, vanadium, chromium, molybdenum, iron, cobalt, nickel, ruthenium, rhodium, palladium, copper and zinc.

7. The process of claim 6 wherein the metal is selected from the group consisting of titanium, iron and chromium.

8. The process of claim 1, wherein the metal compounds are derived from the metals selected from the group consisting of titanium, vanadium, chromium, molybdenum, iron, cobalt, nickel, ruthenium, rhodium, palladium, copper and zinc.

9. The process of claim 1, wherein the metal compounds are selected from the group consisting of carboxylates, acetylacetonates, metal carbonyls, acetates, carbonates, halides, sulfates, metal oxides and metal alkoxides.

10. The process of claim 7, wherein the metal carboxylates are salts of the carboxylic acids which are formed as a result of the separate aldehyde oxidation reaction.

11. The process of claim 1, wherein the preparation of the reaction product from the separate aldehyde oxidation reaction product from the aldehyde oxidation reaction is carried out at temperature of 20 to 100° C.

12. The process of claim 1, wherein the preparation of the reaction product from the separate aldehyde oxidation reaction is carried out at pressures from atmospheric pressure to 1.0 MPa.

13. The process of claim 1, wherein, in the preparation of the reaction product from the separate aldehyde oxidation reaction, the oxygen-containing gas mixture have a proportion of up to 90% by volume, of inert constituents.

14. The process of claim 1 wherein the oxidation of aliphatic straight-chain and β-alkyl-branched aldehydes of 5 to 13 carbon atoms is carried out at temperatures of 20 to 80° C. and at pressures from atmospheric pressure to 1.0 MPa.

15. The process of claim 1 wherein the oxygen-containing gas mixtures used in the oxidation of aliphatic straight-chain and β-alkyl-branched aldehydes of 5 to 13 carbon atoms have a proportion of up to 90% by volume, of inert constituents.

16. The process of claim 1 wherein the aliphatic straight-chain and β-alkyl-branched aldehyde of 5 to 13 carbon atoms which is to be oxidized is used in the preparation of the reaction product from the separate aldehyde oxidation reaction.

17. A catalytic process for preparing aliphatic straight-chain and β-alkyl-branched carboxylic acids of 5 to 3 carbon atoms comprising oxidizing the corresponding aldehydes with oxygen or oxygen-containing gas mixtures at 20 to 100° C. in the liquid phase, wherein the oxidation of the aldehyde is carried out in the presence of a catalyst system which is the reaction product from a separate aldehyde oxidation reaction in which the aldehyde oxidation reaction is carried out in the presence of alkali metal carboxylates or alkaline earth metal carboxylates or a mixture thereof in an amount, calculated as alkali or alkaline earth metal, of 2.5 mmol to 25 mmol per mol of aldehyde used and of 0.25 to 25 ppm of a metal selected from the group consisting of metals of groups 4 to 12 of the Periodic Table, cerium and lanthanum or the corresponding amount of a compound of such a metal or a mixture of such metals and metal compounds, based on the aldehyde used and after said separate aldehyde oxidation reaction, carboxylic acids formed, unreacted starting aldehyde and further volatile constituents are distilled off from the reaction mixture and the distillation residue containing the reaction product is used in the subsequent, actual oxidation of the aldehydes in such an amount that said oxidation of the aldehydes is carried out in the presence of alkali metal carboxylates or alkaline earth metal carboxylates or a mixture, thereof in an amount, calculated as alkali or alkaline earth metal, of 0.5 mmol to 5 mmol per mol of aldehyde used and of 0.05 to 5.0 ppm of a metal of groups 4 to 12 of the Periodic Table, cerium or lanthanum, or the corresponding amount of a compound of such a metal or a mixture of such metals and metal compounds, based on the aldehyde used.

18. The process of claim 17, wherein the preparation of the reaction product from the separate aldehyde oxidation reaction Is carried out in the presence of alkali metal carboxylates or alkaline earth metal carboxylates or a mixture thereof in an amount, calculated as alkali or alkaline earth metal, of 1.5 mmol to 15 mmol per mol of aldehyde used and in the presence of 0.15 to 15 ppm of a metal of groups 4 to 12 of the Periodic Table, cerium or lanthanum or the corresponding amount of a compound of such a metal or a mixture of such metals and metal compounds, based on the aldehyde used.

* * * * *